(12) United States Patent
Thrush et al.

(10) Patent No.: US 9,310,600 B2
(45) Date of Patent: Apr. 12, 2016

(54) DOUBLE FOLD OPTICS

(71) Applicant: Bio-Rad Laboratories, Inc., Hercules, CA (US)

(72) Inventors: Evan Thrush, San Anselmo, CA (US); Evelio Perez, Hercules, CA (US); Steve Swihart, Walnut Creek, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 108 days.

(21) Appl. No.: 14/477,253

(22) Filed: Sep. 4, 2014

(65) Prior Publication Data

US 2015/0070483 A1 Mar. 12, 2015

Related U.S. Application Data

(60) Provisional application No. 61/875,526, filed on Sep. 9, 2013.

(51) Int. Cl.
| | |
|---|---|
| *G03B 15/00* | (2006.01) |
| *G02B 21/36* | (2006.01) |
| *G02B 21/00* | (2006.01) |
| *G01N 21/00* | (2006.01) |
| *G02B 17/02* | (2006.01) |

(52) U.S. Cl.
CPC ............. *G02B 21/361* (2013.01); *G01N 21/00* (2013.01); *G02B 17/023* (2013.01); *G02B 21/0008* (2013.01); *G03B 15/00* (2013.01)

(58) Field of Classification Search
USPC .......................................................... 396/351
See application file for complete search history.

(56) References Cited

U.S. PATENT DOCUMENTS

| | | | | | |
|---|---|---|---|---|---|
| 2,350,793 | A | * | 6/1944 | Mihalyi | 396/447 |
| 3,478,662 | A | * | 11/1969 | Baker | 396/21 |
| 3,563,146 | A | * | 2/1971 | Miller | 396/21 |
| 3,580,150 | A | * | 5/1971 | Watson et al. | 396/21 |
| 3,591,250 | A | | 7/1971 | Feinstein et al. | |
| 3,591,269 | A | * | 7/1971 | Watson et al. | 352/69 |
| 3,620,146 | A | * | 11/1971 | Chandler | 396/21 |
| 5,365,288 | A | * | 11/1994 | Dewald et al. | 353/98 |
| 5,986,810 | A | * | 11/1999 | Webb | 359/618 |
| 6,496,309 | B1 | | 12/2002 | Bliton et al. | |
| 6,512,539 | B1 | * | 1/2003 | Dance et al. | 348/203 |
| 7,129,460 | B1 | * | 10/2006 | Olson et al. | 250/208.1 |
| 2006/0102604 | A1 | | 5/2006 | Dane et al. | |
| 2006/0152799 | A1 | * | 7/2006 | Ri | 359/368 |

(Continued)

OTHER PUBLICATIONS

International Search Report and Written Opinion mailed Dec. 12, 2014, from International Application No. PCT/US2014/054017 (9 pages).

*Primary Examiner* — Rodney Fuller
(74) *Attorney, Agent, or Firm* — Kilpatrick Townsend and Stockton LLP

(57) ABSTRACT

An imaging assembly for the viewing, imaging, and analysis of biological, chemical, and/or biochemical samples in gels or other substrates, in which an adjustable camera and lens module, a reflex mirror, and a focal plane mirror, are configured to bend or fold an optical path in order to image a target region, and where the optical path can be reflected along non-orthogonal angles. The imaging assembly is configured to reduce the overall size of the imaging apparatus due to the angles at which the mirrors and camera and lens assembly are positioned relative to each other, which allows for the imaging of relatively larger samples in the target region.

15 Claims, 3 Drawing Sheets

(56) References Cited

U.S. PATENT DOCUMENTS

| | | | |
|---|---|---|---|
| 2008/0180795 A1* | 7/2008 | Hasegawa | 359/375 |
| 2008/0252904 A1* | 10/2008 | Matsumiya et al. | 356/614 |
| 2011/0006231 A1* | 1/2011 | Betzig et al. | 250/578.1 |
| 2011/0304723 A1* | 12/2011 | Betzig | 348/79 |
| 2012/0268573 A1* | 10/2012 | Schonborn et al. | 348/49 |
| 2014/0015953 A1* | 1/2014 | Turgeman et al. | 348/79 |
| 2014/0043460 A1* | 2/2014 | Hartell et al. | 348/79 |
| 2014/0369575 A1* | 12/2014 | Riopka et al. | 382/127 |
| 2015/0002632 A1* | 1/2015 | Kalkbrenner et al. | 348/46 |

* cited by examiner

DOUBLE FOLD OPTICS

CROSS-REFERENCE TO RELATED APPLICATIONS

The present patent application claims the benefit of priority to U.S. Provisional Patent Application No. 61/875,526, filed on Sep. 9, 2013, the entirety of which is incorporated by reference herein.

FIELD OF THE INVENTION

The present invention generally relates to the field of imaging and apparatus for imaging biological and chemical test and assay results. More specifically, many embodiments are directed to a compact and efficient imaging apparatus for viewing electrophoresis gels, nucleic acid blots, protein blots, or similar biochemical tests and assays at specific increased magnification and resolutions.

BACKGROUND OF THE INVENTION

Instruments and apparatus systems that are used for viewing, recording, and analyzing the results of biological and chemical tests and assays often require instrumentation that can provide specific magnification in order to sufficiently image the target, but require a limited size in order to be useful and useable in a laboratory. For such instrumentation, samples and targets of relatively large sizes create challenges in fitting a sample within the field of view of the instrument, while also keeping the instrument of reasonable and economical size. Moreover, in such instrumentation, the optical path of the imaging apparatus, and the lens speed of the lenses used in the instrumentation, can lead to apparatus that are complex and inefficiently sized. Reduction of the size of the instrumentation by use of smaller zoom lenses, however, can lead to a loss of sufficient sensitivity or field of view so as to adequately image the sample.

Accordingly, there remains a need to provide imaging instrumentation that retains desired magnification, field of view, and focusing and imaging capabilities while remaining relatively compact and efficient for use in chemical and biological laboratories.

SUMMARY OF THE INVENTION

The following presents a simplified summary of some embodiments of the invention in order to provide a basic understanding of the invention. This summary is not an extensive overview of the invention. It is not intended to identify key or critical elements of the invention or to delineate the scope of the invention. Its sole purpose is to present some embodiments of the invention in a simplified form as a prelude to the more detailed description that is presented later.

Embodiments of the imaging assembly include a platform having a target region, a camera and lens module, a reflex mirror, positioned along an optical path incident from the camera and lens module, and a focal plane mirror, positioned along an optical path incident from the reflex mirrors, where the optical path between the camera and lens module and the target region is non-orthogonal, and the optical path has a focal plane in the target region.

Further embodiments are directed toward an imaging assembly, where the assembly is configured to image electrophoresis gels, nucleic acid blots, protein blots, bioluminescent assay results, and/or chemiluminescent assay results. In aspects, the lens of the imaging assembly can have a lens speed of about less than f/2.0, and in further aspects the lens can have a lens speed of about f/1.4.

Some embodiments of the imaging assembly have a reflex mirror positioned at a non-orthogonal orientation relative to the camera and lens module. In aspects, the reflex mirror is oriented relative to the camera and lens module with a yaw angle of about 15° to about 35°. In further aspects, the reflex mirror is oriented relative to the camera and lens module with a yaw angle of about 20° to about 30°. In some embodiments of the imaging assembly, the focal plane mirror is positioned at a orthogonal orientation relative to the reflex mirror. In aspects, the focal plane mirror is positioned at a non-orthogonal orientation relative to the reflex mirror. In further aspects, the focal plane mirror is oriented relative to the reflex mirror with a pitch angle of about 15° to about 25°. In embodiments, the optical path of the imaging assembly has an imaging distance length of about 50 cm to 70 cm, and in other aspects an imaging distance length of about 60 cm.

Further embodiments are directed to an imaging system assembly which includes an imaging assembly having a camera and lens module, a control unit electronically coupled to the camera and lens module and configured to receive data from the camera and lens module, and a user interface, electronically coupled to the control unit and configured to display, transmit, and/or manipulate data received from the camera and lens module. In some aspects, the imaging assembly can further have a platform having a target region, a reflex mirror, positioned along an optical path incident from the camera and lens module, and a focal plane mirror, positioned along an optical path incident from the reflex mirrors. In other aspects, the user interface can be configured to operate the control unit, where the control unit is further configured to send control instructions to the camera and lens module. In further aspects, the imaging system assembly can further include a motor mechanically coupled to the camera and lens module, where the control unit can send control instructions to the motor to alter the working distance of the camera and lens module. In some aspects, the imaging system assembly can have a motor mechanically coupled to the reflex mirror, where the control unit can send control instructions to the motor to alter the orientation angle of the reflex mirror. In other aspects, imaging system assembly can have a motor mechanically coupled to the focal plane mirror, where the control unit can send control instructions to the motor to alter the orientation angle of the focal plane mirror.

BRIEF DESCRIPTION OF THE DRAWINGS

Illustrative aspects of the present disclosure are described in detail below with reference to the following drawing figures

DETAILED DESCRIPTION OF THE INVENTION

Figure 1:
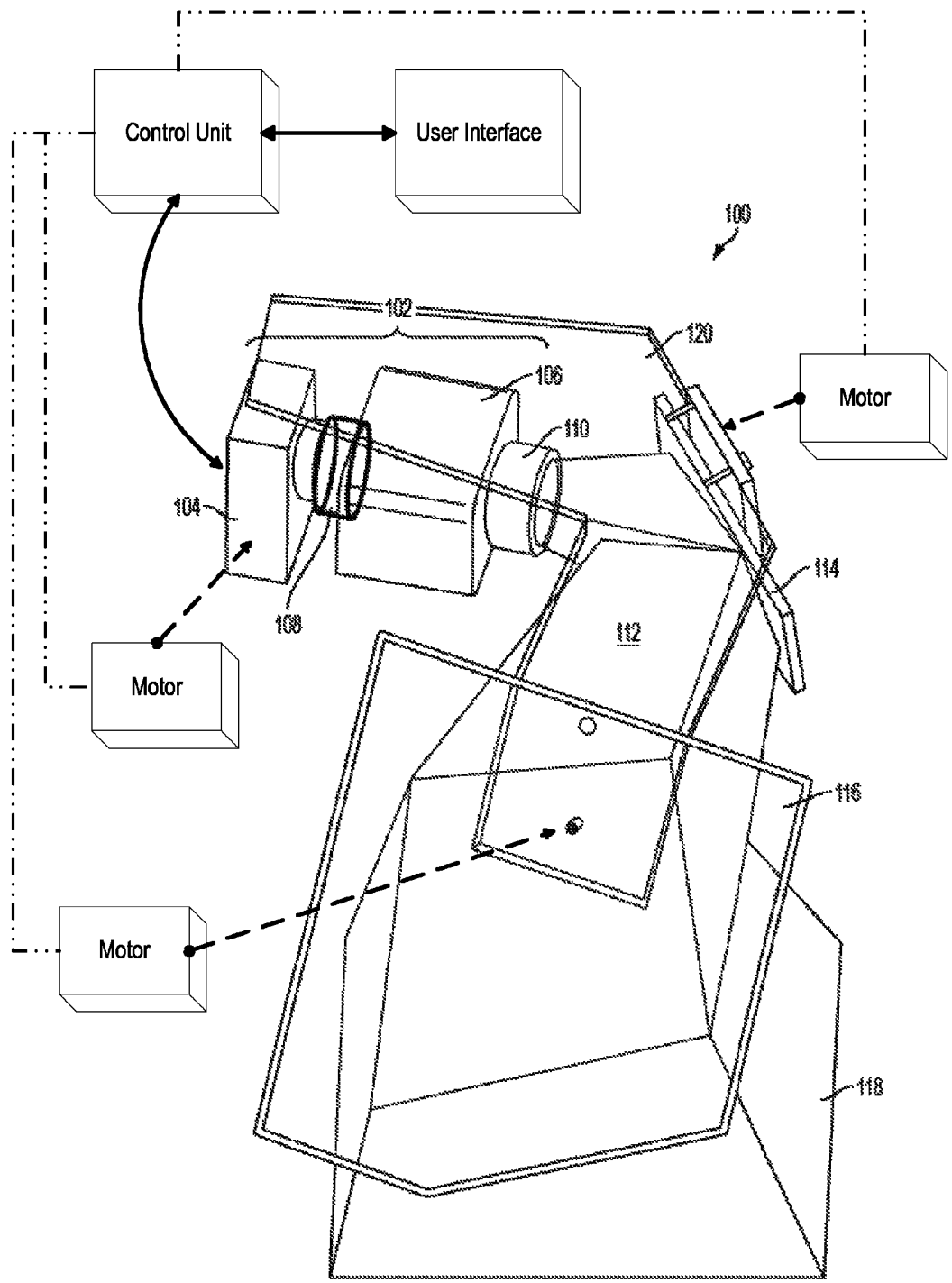
FIG. 1 is an illustration of an optical path range from a camera and lens module reflected along two mirrors into a sample region, according to many embodiments.

Throughout this description for the purposes of explanation, numerous specific details are set forth in order to provide a thorough understanding of the many embodiments disclosed herein. It will be apparent, however, to one skilled in the art that the many embodiments may be practiced without some of these specific details. In other instances, well-known structures and devices are shown in diagram or schematic form to avoid obscuring the underlying principles of the described embodiments.

Imaging systems and apparatus for imaging results from various biological, chemical, and/or biochemical tests and assays often need to accommodate samples of various sizes. Tests and assays such as electrophoresis gels, nucleic acid blots, protein blots, immunochemistry gels, and other such biochemical testing samples can produce samples, gels, and other such membranes which can be from about ten centimeters to about fifty centimeters (10 cm-50 cm) in length along the width or length dimensions of the gel. Such samples can further be chemiluminescent, bioluminescent, and/or externally illuminated. Accordingly, the imaging area of laboratory imaging systems and apparatus can be configured to have a field of view that can encompass the entirety of a sample or a portion of a sample. The optical path of such imaging systems and apparatus may be bent or folded, particularly at non-orthogonal angles, so as to allow for a sufficiently long focal length to achieve the desired field of view in the instrument system or apparatus.

As used herein, the term "non-orthogonal optical path" indicates that a referenced optical path intersects with a reflective and/or refractive surface such that the angle of incidence of the optical path is not at a right angle (i.e. not 90°) in relation to the angle of reflection or angle of refraction. Similarly, as used herein, the term "non-orthogonal orientation" indicates that a referenced reflective and/or refractive surface that intersects with an optical path is positioned and oriented such that optical path does not have an angle of incidence at a right angle in relation to the angle of reflection or angle of refraction (i.e. the surface is not at 45° relative to the incident optical path, and thus does not form a 90° bend in the optical path). Conversely, the term "orthogonal optical path" indicates that the angles of incidence and reflection form a right angle (90°) and the term "orthogonal orientation" indicates that a referenced reflective body is positioned and oriented to cause an incident optical path to reflect at a right angle (i.e. the reflective body is at a 45° angle relative to the incident optical path).

As used herein, the term "yaw angle" refers to the orientation or position of one body relative to another body resulting from translation or rotation along a vertical axis; i.e. the rotation or swiveling of a body to the left or right when viewed from above. A body having a zero (0°) yaw angle is one that is directly in line with the incident direction from which the body is viewed, or in other words, has no rotation leftward or rightward around its vertical axis. As used herein, the term "pitch angle" refers to the orientation or position of one body relative to another body resulting from translation or rotation along a horizontal axis; i.e. the rotation or tilting of a body forward or backward when viewed from above. A body having a zero (0°) pitch angle is one that is plumb straight along its vertical axis, or in other words, has no rotation forward or rearward around its horizontal axis. In reference to both pitch angle and yaw angle, the angle given refers to the angle at the intersection of the optical path and the body between the directional axis of the incident optical path and the portion of the body closer to the direction from which the optical path is incident.

As used herein, the term "focal plane mirror" refers to a mirror positioned along an optical path closest to the target region in which an object is imaged within the field of view of the optical path. As used herein, the term "reflex mirror" refers to a mirror positioned along an optical path closer to the camera and/or lens assembly or module, which captures images from along that optical path, than a focal plane mirror proximate to the target region imaged by the camera and lens module.

In embodiments of an optical system used to image samples, the imaging system and apparatus can have an imaging area that is twenty-five centimeters by twenty centimeters (25 cm×20 cm) in size. Some embodiments of the optical system may have an imaging area that can be from about nine centimeters (9 cm) to about thirty-five centimeters (35 cm) along either the width and/or length of the imaging area. An imaging area of this size can accommodate sample gels and membranes resulting from biochemical tests and assays, in particular sample gels or membranes which are from about ten centimeters to about fifty centimeters (10 cm-50 cm) in length along the width or length dimensions of the sample. Accordingly, the optical system includes a camera and lens module ("CLM") to image and record objects in the field of view. The CLM can be constructed of a CCD camera and a motorized zoom lens. In embodiments, the CCD camera may be cooled by a dedicated cooling system, or while in other embodiments the CCD camera may be uncooled, i.e. unconnected to a dedicated cooling system.

In embodiments, in order to improve the image obtained by the CLM, it is desirable to have a zoom lens that can zoom into a region of interest of a sample for higher pixel sampling. A zoom lens for such an embodiment requires an lens speed (also referred to as the f-number) of about less than 2 (about <f/2.0). In further embodiments, the lens can have a lens speed of about f/1.4. In embodiments, the focal length of the CLM can be in the range of about five millimeters to about one hundred millimeters (5 mm-100 mm), which may vary depending on the magnification required by the imaging system and the corresponding working distance. In some embodiments, the lens has a field of view of about twenty-seven centimeters (27 cm), which allows that optical instrumentation to have a sufficiently wide/large field of view so as to cover a twenty-five centimeters by twenty centimeters (25 cm×20 cm) imaging area. In various embodiments, the field of view of a zoom lens can be variable and in the range from about five to about thirty-five centimeters (5 cm-35 cm). A change in the field of view of the optical instrumentation can be caused by changing the focal length of the zoom lens, which is accomplished by changing the optical design and relative position of the lens elements, or groups of lens elements. A motor internal to the camera, a camera housing, or a lens housing can be used to adjust the distance between the lens elements. In embodiments, the lens elements of the zoom lens can be changed by about four to five millimeters (4 mm-5 mm) from each other.

Commercially available zoom lenses that meet the lens speed and field of view required as described above are often large and have a minimum working distance that requires the working distance of the lens and associated camera to be at least about thirty centimeters (30 cm), and can also have minimum working distance requirements of fifty centimeters (50 cm) or one hundred centimeters (100 cm). If implemented with a straight optical path, the resulting imaging system is of a size typically not amenable to or feasible with the space available in a lab workspace. Thus, in embodiments, folding the optical path at least twice with at least one non-orthogonal angle allows for use of lenses with desired lens speed and field of view, while managing the corresponding working distance within a size-efficient framework. In such embodiments, the lens can have an imaging distance of about sixty centimeters (60 cm), but be more compact in construction than an implementation with a straight optical path having an equivalent or shorter imaging distance. In further embodiments, the lens can have an imaging distance of about fifty centimeters to about seventy centimeters (50 cm-70 cm), and in further embodiments, the lens can have an imaging distance of about forty centimeters to one hundred centimeters (40 cm-100 cm). Yet further embodiments can have lenses with an imaging distance at any increment or gradient at or within these ranges. In such embodiments, while the zoom lens can change the field of view observed by the CLM, the length of the optical path does not change.

In some embodiments of the imaging assembly, the space occupied by the imaging assembly is reduced and minimized by folding the optical path between the camera and lens assembly and the target area. Minimizing the bench space taken up by the imaging assembly product is advantageous in order to allow for use of the apparatus in compact spaces in laboratories. In embodiments, the optical path of the imaging assembly is folded by use of at least two mirrors (a reflex mirror and a focal plane mirror) located above the target area, having yaw and pitch angles relative to the related camera and lens module such that the height and/or width of the imaging assembly is reduced by approximately the sum of the distance from the camera and lens module to the reflex mirror and the distance from the reflex mirror to the focal plane mirror. In particular, the at least two mirrors and the CLM are oriented relative to each other with at least one non-orthogonal angle to efficiently reduce the height and/or width of the imaging assembly. Accordingly, the folding, bending, and/or tilting of the optical path beam can further increase the path length, or decrease the overall size of the imaging assembly, within a desired and/or constrained volume of space.

While the many embodiments disclosed herein are generally directed to an efficient imaging apparatus with a compact form factor for imaging chemiluminescent or bioluminescent samples, the imaging apparatus described herein can be used for any application where a wide field of view and compact imaging assembly, with similar or analogous lens speed and focal length requirements, would be appropriate or advantageous.

FIG. 1 is an illustration of an optical path range from a camera and lens module reflected along two mirrors into a sample region 100, according to many embodiments. In embodiments, the camera and lens module ("CLM") 102 is connected to a CLM interface (not shown), which is in turn electronically connected to non-transitory computer readable media, to which images captured by the CLM 102 are transmitted. Embodiments of the CLM 102 can include a camera 104, lens housing 106, lens assembly 108, and lens encasement 110. The lens housing 106 at least partially contains and protects the lens assembly 108, though the lens assembly 108 can extend out from the lens housing 106 either toward the camera 104 or into the lens encasement. The lens encasement 110 can enclose and protect the portion of the lens assembly 108 extends from the front of the lens housing 106 and can span the range over which the lens assembly 108 can zoom. A controllable motorized assembly can further reside in the lens housing 106 and change the distance between groupings of lenses in the lens assembly 108 to change the area within the field of view by the lens assembly 108. In particular embodiments, the lens assembly 108 can be about fifteen centimeters (15 cm) in length and about two inches (2") in diameter. The CLM 102 is oriented and positioned such that its optical path 112 intersects with at least one reflex mirror 114 and a focal plane mirror 116 and covers a target region 118, from which imaging data of samples are collected. (As illustrated in FIG. 1, the focal plane mirror 116 is represented as transparent to allow for visualization of other aspects of the illustration.)

The optical path 112 is viewed as originating from the lens. Proceeding from the CLM 102, the optical path 112 intersects with a reflex mirror 114. In embodiments, the reflex mirror 114 is positioned, relative to the CLM 102, at about 25 cm distant from the CLM 102. In further embodiments, the reflex mirror 114 can be from about 20 cm to about 30 cm distant from the CLM 102. In yet further embodiments, the reflex mirror 114 can be from about 15 cm to about 35 cm distant from the CLM 102. The reflex mirror 114 has a pitch angle of 0° and a yaw angle of about 20°; in other words, the reflex mirror 114 is not rotated in any direction around a horizontal axis (i.e. is plumb straight and is not tilted) and is rotated such that a 20° angle is formed between the directional axis of incident optical path 112 and the horizontal plane of the reflex mirror 114 proximate to the CLM 102. In embodiments, the reflex mirror 114 can have a yaw angle of 22.5°. In some embodiments, the reflex mirror 114 can have a yaw angle of about 25° or a yaw angle of about 30°. In further embodiments, the reflex mirror 114 can have a yaw angle of from about 15° to about 35°. In yet further embodiments, the reflex mirror 114 can have a yaw angle of about 1° to about 44° or a yaw angle of about 46° to about 89°. In some embodiments, the reflex mirror 114 can have a pitch angle of about 1° to about 44° or a pitch angle of about 46° to about 89° (i.e. tilted forward), where the pitch angle is measured as between the directional axis of incident optical path 112 and the vertical plane of the reflex mirror 114 proximate to the CLM 102. In such embodiments, the reflex mirror 114 is in a non-orthogonal orientation. Accordingly, the reflection incident from the CLM 102 off of the reflex mirror 114 is a non-orthogonal optical path 112.

In alternative embodiments, the reflex mirror 114 is positioned along its vertical axis in an orthogonal orientation relative to the CLM 102 (i.e. at a yaw angle of 45° relative to the optical path 112 incident from the CLM 102) such that optical path 112 reflects off of the reflex mirror at a right angle (90°). In such embodiments, with the reflex mirror 114 in an orthogonal orientation, any subsequent reflex mirror or focal plane mirror 116 can be in a non-orthogonal or orthogonal orientation. Providing a reflex mirror 114 in an orthogonal orientation further allows for optical instrumentation where a subsequent reflex mirror or a focal plane mirror 116 which is non-orthogonal along both pitch and yaw axes. In either orthogonal or non-orthogonal orientations, for both pitch and yaw angles, the reflex mirror 114 cannot be positioned at an angle that results in the CLM 102 being captured within the field of view of the optical path 112. Further, in either orthogonal or non-orthogonal orientations, for both pitch and yaw angles, the reflex mirror 114 should not be positioned at an angle that results in the reflex mirror 114 collecting significant amounts of dust which can adversely obscure the image captured from the target region 118.

The optical path 112 reflects from the reflex mirror 114 to a focal plane mirror 116. In embodiments, the focal plane mirror 116 is positioned, relative to the reflex mirror 114, at about 23 cm distant from the reflex mirror 114. In further embodiments, the focal plane mirror 116 can be from about 18 cm to about 28 cm distant from the reflex mirror. In further embodiments, the focal plane mirror 116 can be from about 13 cm to about 33 cm distant from the reflex mirror. The focal plane mirror 116 has a pitch angle of 45° and a yaw angle of about 0°; in other words, the focal plane mirror 116 is rotated forward around its horizontal axis such that 45° angle is formed between the directional axis of incident optical path 112 and the plane of the focal plane mirror 116 proximate to the reflex mirror 114 (i.e. tilted forward), and is not rotated (i.e. is perpendicular) around the its vertical axis relative to the directional axis of the optical path 112 incident from the reflex mirror 114. In such embodiments, where the focal plane mirror 116 is in an orthogonal orientation relative to the optical path 112 incident from the reflex mirror 114 with respect to the yaw angle, the optical path 112 reflects off of the focal plane mirror at a 90° angle down toward the target region. In some embodiments, the focal plane mirror 116 can have a yaw angle of about 1° to about 44° or a yaw angle of about 46° to about 89°. In such embodiments, the focal plane mirror 116 is in an orthogonal orientation with respect to the pitch angle. However, the overall optical path 112 originating from the CLM 102 and reflecting off of the reflex mirror 114 and subsequently reflecting off of the focal plane mirror is a non-orthogonal optical path 112.

In alternative embodiments, the focal plane mirror 116 is positioned in a non-orthogonal orientation relative to the reflex mirror 114 such that the optical path 112 does not reflect off of the focal plan mirror at a right angle (90°). In such embodiments, the focal plane mirror 116 can have a pitch angle of about 1° to about 44° or a pitch angle of about 46° to about 89°, where the pitch angle is measured as between the directional axis of incident optical path 112 and the plane of the reflex mirror proximate to the reflex mirror 114. In some embodiments, the focal plane mirror 116 can have a pitch angle of about 1° to about 44° or a pitch angle of about 46° to about 89°. In yet further embodiments, the focal plane mirror 116 can have a pitch angle of about 15° to about 25°. In either orthogonal or non-orthogonal orientations, for both pitch and yaw angles, the focal plane mirror 116 cannot be positioned at an angle that results in the CLM 102 being captured within the field of view of the optical path 112. Further, in either orthogonal or non-orthogonal orientations, for both pitch and yaw angles, the focal plane mirror 116 should not be positioned at an angle that results in the focal plane mirror 116 collecting significant amounts of dust which can adversely obscure the image captured from the target region 118.

In embodiments, the reflex mirror 114 and/or the focal plane mirror 116 are planar mirrors which can be circular mirrors, rectangular mirrors, and/or irregularly shaped mirrors. The reflex mirror 114 and/or the focal plane mirror 116 can be shaped or cut to accommodate the space of the imaging system, or to allow access to the interior space of the imaging system by a user. The target region 118, where samples are located for imaging, is covered by the field of view of the optical path 112. In embodiments, a sample placed in the target region 118 and imaged can have a length of about 20 cm to about 30 cm and a width of about 20 cm to about 30 cm. In further embodiments, a sample placed in the target region 118 and imaged can have a length of about 10 cm to about 50 cm and a width of about 10 cm to about 50 cm. In some embodiments, the focal plane mirror 116 can be larger in width and/or diameter than the reflex mirror 114. In particular embodiments, the focal plane mirror 116 can be from about two time (2×) to three times (3×) larger than the reflex mirror 114. In some embodiments, the imaging apparatus includes a support structure 120 from which the CLM 102, reflex mirror 114, and/or the focal plane mirror 116 can be mounted. The support structure 120 can be positioned above the general area of the optical path 112 and target region 118 and positioned so as to not interrupt the optical path 112 and not be captured within the field of view of the CLM 102 collecting imaging data. (As illustrated in FIG. 1, the support structure 120 is represented as transparent to allow for visualization of other aspects of the illustration.)

Figure 2:
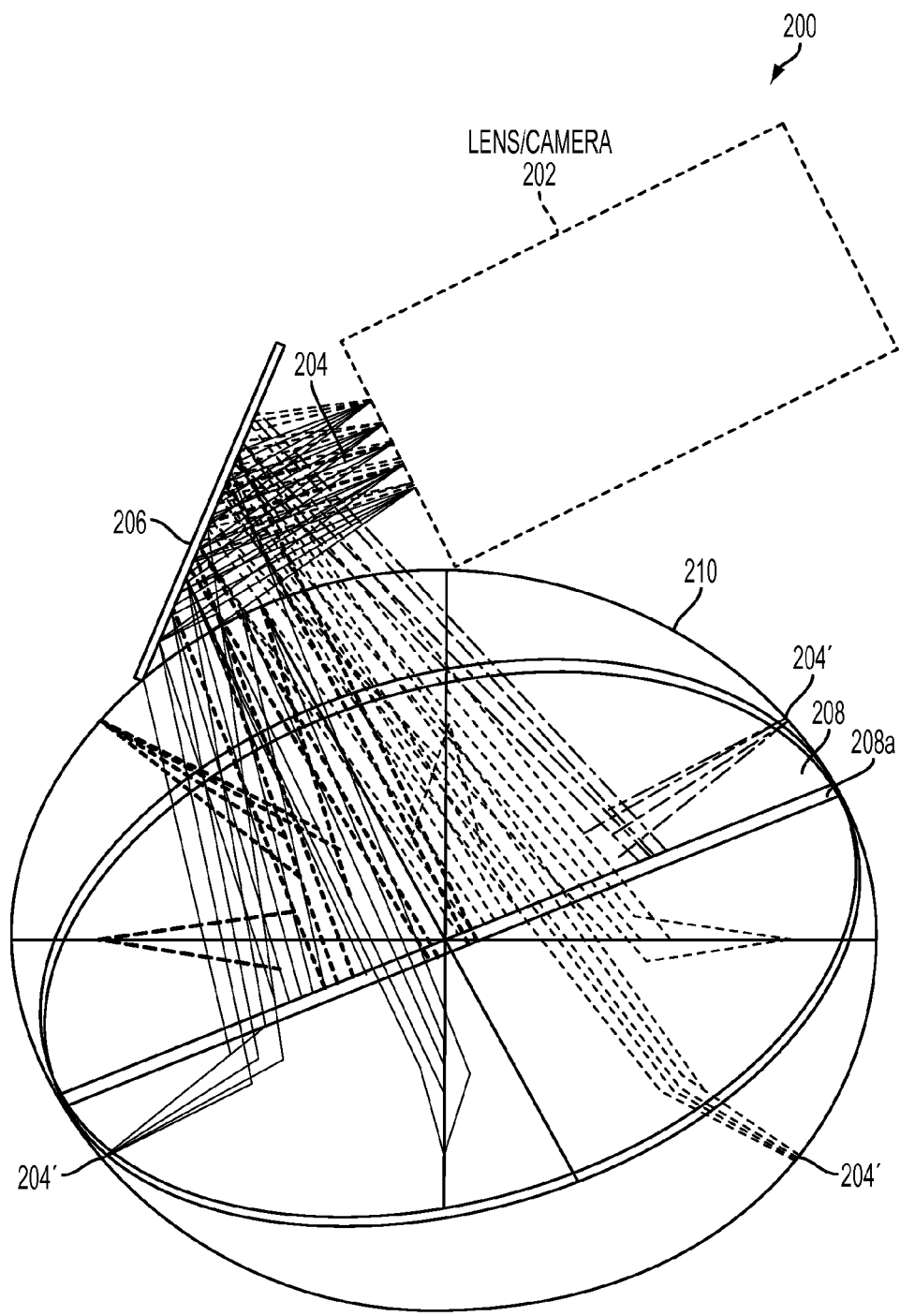
FIG. 2 is an illustration of optical paths from a camera and lens module reflected and refracted along two mirrors into a sample region, according to many embodiments.

FIG. 2 is an illustration of optical paths from a camera and lens module reflected and refracted along two mirrors into a sample region 200, particularly illustrating the perimeter of the field of view covering a target region. A CLM 202 can have multiple optical paths 204 that are projected from the CLM 202 and intersect with a reflex mirror 206, and are further redirected toward a focal plane mirror 208. The reflex mirror 206 can have a non-orthogonal orientation, which as in the embodiment illustrated, can have a yaw angle of 30° relative to the axes of the optical paths 204 emerging from the CLM 202. In other words, the reflex mirror 206 can be rotated around its vertical axis such that a 30° is formed at the points of intersection between the incident direction of the optical paths 204 and the plane defined by the surface of the reflex mirror 206 closer to the CLM 202. The focal plane mirror 208 can be oriented relative to the reflex mirror 206 with a pitch angle that reflects and directs the optical paths 204 incident from the reflex mirror downward toward the sample region 210. In other words, the focal plane mirror 208 can be rotated around its horizontal axis 208a such that its upper portion is tilted forward, i.e. toward the reflex mirror 206. The optical path 204 reflecting off of the focal plane mirror 208 (and particularly reflecting along the horizontal axis 208a of the focal plane mirror 208) project downward toward the sample region 210 and end at optical path terminus points 204'. The terminus points 204' indicate the perimeter of the field of view observable by the CLM 202 at a given orientation and degree of zoom. The terminus points 204' can be co-terminus with the perimeter of the sample region 210, can lie within the sample region 210, or lie outside the sample region. In aspects, when a terminus point 204' lies inside the perimeter of the sample region 210, portions of the sample region beyond the given terminus point 204' are not within the field of view of the CLM 202, and those portions are thus not imaged. In aspects, when a terminus point 204' lies outside the perimeter of the sample region 210, portions of the sample field of view before the given terminus point 204' may not contain sample gel or membrane to be imaged within the sample region 210. The locations of the terminus points 204' relative to or within the sample region 210 can be adjusted by modifying the pitch and/or yaw angles of the reflex mirror 206 and/or the focal plane mirror 208. Further, the locations of the terminus points 204' relative to or within the sample region 210 can be adjusted by changing the zoom factor of the lens within the CLM 202.

Figure 3:
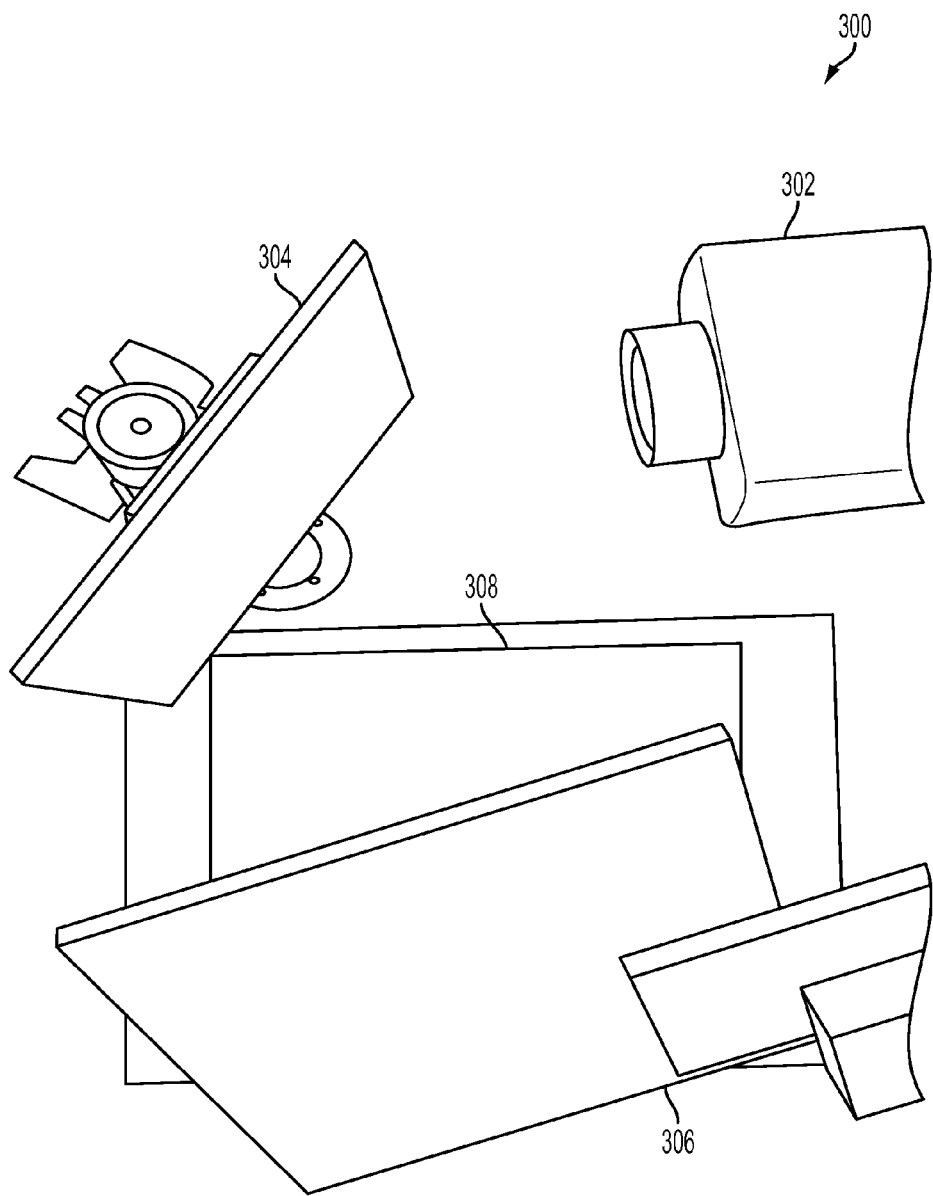
FIG. 3 is an image of a imaging assembly having a camera and lens module, a reflex mirror, and a focal plane mirror, positioned over a sample region, according to an embodiment.

FIG. 3 is a top view illustration of a imaging assembly set-up having a camera and lens module, a reflex mirror, and a focal plane mirror, positioned over a sample region 300 according to an embodiment. An optical path originating from the CLM 302 intersects with a reflex mirror 304, having a yaw angle of about 30° relative to the CLM 302. The optical path is reflected and proceeds to focal plane mirror 306, positioned relative to the reflex mirror 304 with a pitch angle of about 20° (i.e. tilted forward). The sample region 308 is within the field of view of the CLM 302, the optical path being redirected (in this set-up, downward) to image the sample region 308 by the focal plane mirror 306. The pictured imaging apparatus can further be contained within a housing surrounding the CLM 302, reflex mirror 304, focal plane mirror 306, sample region 308, and their respective supporting components.

In further embodiments, the optical path of an imaging assembly may be folded or bent with more than two mirrors. In such embodiments, the optical path projected from a CLM can intersect with and reflect off of a first reflex mirror, subsequently intersect with and reflect off of a second reflex mirror, further intersect with and reflect off of a focal plane mirror, and thus project a field of view over a target region. In such embodiments, the first reflex mirror, second reflex mirror, and focal plane mirror can each, individually and alternatively, have a yaw angle of about 1° to about 89°. Similarly, in such embodiments, the first reflex mirror, second reflex mirror, and focal plane mirror can each, individually and alternatively, have a pitch angle of about 1° to about 89°. In some embodiments, at least one of the yaw angle or pitch angle of the first reflex mirror, second reflex mirror, or focal plane mirror can have a non-orthogonal orientation, thus resulting in an imaging system having a non-orthogonal optical path. Further alternative embodiments may employ any number of reflex mirrors in combination with a CLM and focal plane mirror, so long as the configuration of the imaging assembly meets the size and form factor requirements of the overall instrumentation and apparatus.

In some embodiments, the reflex mirror is adjustable along both its yaw angle and pitch angle, while in other embodiments the reflex mirror is only adjustable along its yaw angle. In some embodiments, the focal plane mirror is adjustable along both its yaw angle and pitch angle, while in other embodiments the focal plane mirror is only adjustable along its pitch angle. The angles the reflex mirror and focal plane mirror are chosen to fit within any given housing or to conform to a needed form factor. For example, an imaging apparatus and system which is required to have a relatively long length and minimized depth and width may have a reflex mirror with a particularly acute yaw angle. Conversely, an imaging apparatus and system which is required to have a relatively tall form factor may have a focal plane mirror with a particularly obtuse pitch angle. Variations and extensions thereof can permit for the construction of further alternative configurations, based upon the pitch angles and yaw angles for the reflex mirrors and focal plane mirrors disclosed herein.

In some embodiments, the CLM can be moved within an imaging assembly by a motor controlled by a control unit, where the motor can be mechanically coupled to the CLM and change the working distance by altering the position of the CLM. In other embodiments, the angle of either or both of the reflex mirror and the focal plane mirror can be moved within an imaging assembly by one or more motors controlled by the control unit, where the one or more motors can be mechanically coupled to either or both of the reflex mirror and the focal plane mirror change the angle at which either or both of the reflex mirror and the focal plane mirror are oriented, or alter the working distance by altering the position of either or both of the reflex mirror and the focal plane mirror. In other embodiments, any or all of the CLM, reflex mirror, and focal plane mirror can have their working distance and or orientation angle manually altered by an operator.

As provided herein, the CLM which captures images of samples located in the target region is electronically coupled with a CLM interface and/or non-transitory computer readable mediums, such as microprocessors. A CLM and/or CLM interface can be electrically coupled to a microprocessor (or equivalent) by wires or by wireless means and thereby send imaging data signals to the microprocessor. The coupled microprocessor which collects the imaging data from the CLM and/or CLM interface can further relay collected information to other non-transitory computer readable mediums, and/or run calculations on collected data and relay the calculated result to a user-operable and/or user-readable display. The imaging data captured by the CLM and/or CLM interface can be filtered by the microprocessor (either through hardware or software) to analyze or base calculations on specific wavelengths of light emitted by a sample gel or membrane, and/or specific wavelengths of light used to illuminate a sample gel or membrane. In such embodiments, an imaging system can include a CLM, a control unit electronically coupled to the CLM which can receive data from and send control instructions to the CLM, and a user interface electronically coupled to the control unit and configured to display, transmit, and/or manipulate such data, where the user interface can further operate the control unit to send control instructions to the CLM, which in some aspects can be instructions to alter the working distance of the CLM via a motor. In further embodiments, the imaging system a control unit can send control instructions to either or both of the reflex mirror and the focal plane mirror, which in some aspects can be can be instructions to alter the orientation angle of either or both of the reflex mirror and the focal plane mirror via one or more motors.

The above description is illustrative and is not restrictive, and as it will become apparent to those skilled in the art upon review of the disclosure, that the present invention may be embodied in other specific forms without departing from the essential characteristics thereof. For example, any of the aspects described above may be combined into one or several different configurations, each having a subset of aspects. Further, throughout the foregoing description, for the purposes of explanation, numerous specific details were set forth in order to provide a thorough understanding of the invention. It will be apparent, however, to persons skilled in the art that these embodiments may be practiced without some of these specific details. These other embodiments are intended to be included within the spirit and scope of the present invention. Accordingly, the scope of the invention should, therefore, be determined not with reference to the above description, but instead should be determined with reference to the following and pending claims along with their full scope of legal equivalents.

What is claimed is:

1. An imaging assembly comprising:
a platform having a target region;
a camera and lens module;
a reflex mirror, positioned along an optical path incident from the camera and lens module, wherein the reflex mirror is oriented relative to the camera and lens module with a yaw angle of about 15° to about 35°; and
a focal plane mirror, positioned along an optical path incident from the reflex mirror, wherein the focal plane mirror is oriented relative to the reflex mirror with a pitch angle of about 15° to about 25°, the optical path between the camera and lens module and the target region being non-orthogonal, having an imaging distance length of about 50 cm to about 70 cm, and having a focal plane in the target region.

2. An imaging assembly according to claim 1, wherein the assembly is configured to position electrophoresis gels, nucleic acid blots, protein blots, bioluminescent assays, and/or chemiluminescent assays in the target region.

3. An imaging assembly according to claim 1, wherein the lens has a lens speed of about less than f/2.0.

4. An imaging assembly according to claim 1, wherein the lens has a lens speed of about f/0.4.

5. An imaging assembly according to claim 1, wherein the reflex mirror is positioned at a non-orthogonal orientation relative to the camera and lens module.

6. An imaging assembly according to claim 1, wherein the reflex mirror is oriented relative to the camera and lens module with a yaw angle of about 20° to about 30°.

7. An imaging assembly according to claim 1, wherein the focal plane mirror is positioned at a orthogonal orientation relative to the reflex mirror.

8. An imaging assembly according to claim 1, wherein the focal plane mirror is positioned at a non-orthogonal orientation relative to the reflex mirror.

9. An imaging assembly according to claim 1, wherein the optical path has an imaging distance length of about 60 cm.

10. An imaging system assembly comprising:
   an imaging assembly comprising a camera and lens module and a target region, wherein an optical path between the camera and lens module and the target region is non-orthogonal, has an imaging distance length of about 50 cm to about 70 cm, and has a focal plane in the target region;
   a control unit, electronically coupled to the camera and lens module and configured to receive data from the camera and lens module; and
   a user interface, electronically coupled to the control unit and configured to display, transmit, and/or manipulate data received from the camera and lens module.

11. An imaging system assembly according to claim 10, the imaging assembly further comprising:
   a platform having a target region;
   a reflex mirror, positioned along an optical path incident from the camera and lens module, wherein the reflex mirror is oriented relative to the camera and lens module with a yaw angle of about 15° to about 35°; and
   a focal plane mirror, positioned along an optical path incident from the reflex mirror, wherein the focal plane mirror is oriented relative to the reflex mirror with a pitch angle of about 15° to about 25°.

12. An imaging system assembly according to claim 10, the user interface being further configured to operate the control unit, and the control unit being further configured to send control instructions to the camera and lens module.

13. An imaging system assembly according to claim 10, further comprising a motor mechanically coupled to the camera and lens module, the control unit being further configured to send control instructions to the motor to alter the working distance of the camera and lens module.

14. An imaging system assembly according to claim 10, further comprising a motor mechanically coupled to the reflex mirror, the control unit being further configured to send control instructions to the motor to alter the orientation angle of the reflex mirror.

15. An imaging system assembly according to claim 10, further comprising a motor mechanically coupled to the focal plane mirror, the control unit being further configured to send control instructions to the motor to alter the orientation angle of the focal plane mirror.

* * * * *